US012651336B2

(12) United States Patent
Teichmann et al.

(10) Patent No.: US 12,651,336 B2
(45) Date of Patent: Jun. 9, 2026

(54) COMPUTER-ASSISTED MEDICAL DIAGNOSIS SYSTEM AND METHOD

(71) Applicant: Siemens Healthineers AG, Forchheim (DE)

(72) Inventors: Marvin Teichmann, Erlangen (DE); Andre Aichert, Erlangen (DE); Rico Brendtke, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 318 days.

(21) Appl. No.: 18/364,106

(22) Filed: Aug. 2, 2023

(65) Prior Publication Data

US 2024/0046468 A1  Feb. 8, 2024

(30) Foreign Application Priority Data

Aug. 5, 2022  (EP) ..................................... 22189032

(51) Int. Cl.
 *G06T 7/00* (2017.01)
 *G16B 20/00* (2019.01)
 (Continued)

(52) U.S. Cl.
 CPC ............ *G06T 7/0012* (2013.01); *G16B 20/00* (2019.02); *G16B 40/20* (2019.02); *G16H 10/60* (2018.01);
 (Continued)

(58) Field of Classification Search
 CPC ......... G06T 7/0012; G06T 2207/20084; G06T 2207/30024; G06T 2207/30028;
 (Continued)

(56) References Cited

U.S. PATENT DOCUMENTS

2021/0090694 A1 * 3/2021 Colley ................... G16B 30/00
2021/0125686 A1  4/2021 Liu et al.
 (Continued)

FOREIGN PATENT DOCUMENTS

CA  3133826 A1  10/2020
EP  4216231 A1  7/2023
EP  4239589 A1  9/2023

OTHER PUBLICATIONS

Hildebrand, A.L. et al.: "Artificial intelligence for histology-based detection of microsatellite instability and prediction of response to immunotherapy in colorectal cancer", in: Cancers, 13(3):391, 2021.
 (Continued)

*Primary Examiner* — John R Wallace
(74) *Attorney, Agent, or Firm* — Harness, Dickey & Pierce, P.L.C.

(57) ABSTRACT

A computer-implemented diagnostic-assistance system for medical applications, comprises: an artificial intelligence neural network configured to classify images of an obtained image dataset according to a set of classes; a confidence module configured to generate a confidence measure associated with each of the classified images; a tagging module configured to generate, for the patient, a diagnostic signal based on the generated confidence measures associated with the classified images, wherein the diagnostic signal for the patient is tagged as conclusive if a processed combination of the confidence measures fulfills a condition and tagged as inconclusive if the processed combination of the confidence measures does not fulfill the condition; and an output interface configured to output the diagnostic signal, wherein if the diagnostic signal is conclusive the classification result is released, and if the diagnostic signal is inconclusive an additional diagnostic analysis is triggered.

19 Claims, 3 Drawing Sheets

(51) Int. Cl.
　　*G16B 40/20* 　　　(2019.01)
　　*G16H 10/60* 　　　(2018.01)
　　*G16H 50/20* 　　　(2018.01)
(52) U.S. Cl.
　　CPC ... *G16H 50/20* (2018.01); *G06T 2207/20084*
　　　(2013.01); *G06T 2207/30024* (2013.01); *G06T*
　　　　　　　　　　　　　　*2207/30028* (2013.01)
(58) Field of Classification Search
　　CPC ........ G16B 20/00; G16B 40/20; G16H 10/60;
　　　　　　　　　　　　　　　　　　G16H 50/20
　　See application file for complete search history.

(56) References Cited

U.S. PATENT DOCUMENTS

| | | | |
|---|---|---|---|
| 2021/0321932 A1* | 10/2021 | Borsody | .............. A61B 5/4076 |
| 2022/0068444 A1* | 3/2022 | Prosky | ................ G06F 18/2415 |
| 2022/0189150 A1* | 6/2022 | Bentaieb | .............. G06V 10/806 |
| 2022/0319000 A1 | 10/2022 | Teichmann et al. | |
| 2023/0230704 A1 | 7/2023 | Adiyoso et al. | |
| 2023/0282011 A1 | 9/2023 | Teichmann et al. | |

OTHER PUBLICATIONS

A. Kendall and Y. Gal; "What uncertainties do we need in bayesian deep learning for computer vision?"; Advances in neural information processing systems; pp. 5574-5584; 2017.

Schaumberg, A.J. et al.: "H&E-stained whole slide image deep learning predicts spop mutation state in prostate cancer.", in: BioRxiv, p. 064279, 2017.

Coudray N. et al.: "Classification and mutation prediction from non-small cell lung cancer histopathology images using deep learning," Nat. Med., vol. 24, No. 10, pp. 1559-1567, 2018, doi:10.1038/s41591-018-0177-5.

Stjepanovic, N. et al.: "Hereditary gastrointestinal cancers: Esmo clinical practice guidelines for diagnosis, treatment and follow-up", in: Annals of Oncology, 30(10):1558-1571, 2019.

Kather J.N. et al.: "Deep learning can predict microsatellite instability directly from histology in gastrointestinal cancer". Nature medicine, 25(7):1054-1056, 2019.

Charoenphakdee, N.; Cui, Z. et al.: "Classification with rejection based on cost-sensitive classification", in: In International Conference on Machine Learning, pp. 1507-1517. PMLR, 2021.

Diggs, L.P. et al.:"Utility of pd-I1 immunohistochemistry assays for predicting pd-1/pd-I1 inhibitor response", in: Biomarker research, 5(1):1-6, 2017.

Nagpal K. et al.:"Development and validation of a deep learning algorithm for improving gleason scoring of prostate cancer" NPJ digital medicine, 2(1):1-10, 2019.

Kather, J.N. et al.: "Pan-cancer image-based detection of clinically actionable genetic alterations", in: Nat Cancer. Aug. 2020 ; 1(8): 789-799. doi:10.1038/s43018-020-0087-6.

Dedeurwaerdere, F. et al.: "Comparison of microsatellite instability detection by immunohistochemistry and molecular techniques in colorectal and endometrial cancer", in: Scientific reports, 11(1):1-15, 2021.

Chenri, N.; Charoenphakdee, N. et al.: "On the calibration of multiclass classification with rejection", in: Advances in Neural Information Processing Systems, 32, 2019.

Teichmann, Marvin et al:"End-to-end Learning for Image-based Detection of Molecular Alternations in Digital Pathology" (https://arxiv.org/pdf/2207.00095); XP091260408; Jun. 30, 2022.

Echle, A. et al.: "Clinical-grade detection of microsatellite instability in colorectal tumors by deep learning", in: Gastroenterology, 159(4):1406-1416, 2020.

Umar, A. et al.: "Revised bethesda guidelines for hereditary nonpolyposis colorectal cancer (lynch syndrome) and microsatellite instability", in: Journal of the National Cancer Institute, 96(4):261-268, 2004.

Zhang et al. : "Understanding deep learning requires rethinking generalization".

Knight Diagnostic Laboratories. Microsatellite instability (msi) with immunohistochemistry (ihc). https://knightdxlabs.ohsu.edu/home/test-details?id=Microsatellite+Instability(MSI)+with+Immunohistochemistry+(IHC)+ (Stand: Apr. 28, 2022).

Limburg, P.J. et al.: "Prevalence of alterations in dna mismatch repair genes in patients with young-onset colorectal cancer", in: Clinical Gastroenterology and Hepatology, 9(6):497-502, 2011.

Ghesu et al., "Quantifying and leveraging predictive uncertainty for medical image assessment", Medical Image Analysis, 2021, pp. 1-28.; 2021.

\* cited by examiner

COMPUTER-ASSISTED MEDICAL DIAGNOSIS SYSTEM AND METHOD

CROSS-REFERENCE TO RELATED APPLICATION(S)

The present application claims priority under 35 U.S.C. § 119 to European Patent Application No. 22189032.0, filed Aug. 5, 2022, the entire contents of which are incorporated herein by reference.

FIELD

One or more example embodiments of the present invention relate to a computer-assisted diagnosis system for medical applications in digital pathology. In particular, one or more example embodiments of the present invention relate to the use of artificial neural networks for diagnostic decision support.

One or more example embodiments of the present invention may be applied to the prediction of molecular biomarkers in tissue samples, in particular for cancer detection, but the principles of one or more example embodiments of the present invention have a broader scope.

BACKGROUND

The development of new technologies together with the irruption of big data in medical applications has led to the concept of precision medicine, where a medical diagnosis can lead to different prognosis and targeted treatment for different patents on a case by case basis. In order to process and interpret large volumes of data computer-aided applications and, in particular, artificial intelligence, machine learning and deep learning are nowadays well-established tools whose presence in the medical and clinical workflows is steadily increasing.

In the particular field of cancer diagnosis and treatment, image-based artificial intelligence is used not only to detect tumors in tissue samples, but also to extract and interpret more subtle information from digitized histopathology samples. Personalized medicine and patient-specific therapies have benefitted from a growing understanding of the underlying biological and molecular mechanisms behind cancer.

Molecular alterations or molecular biomarkers have been associated with certain cases of cancer and their presence or absence is an important indicator to decide on the therapies to follow. Different tests adapted to the different biomarkers have been developed.

Nowadays next-generation sequencing (NGS), which is based on DNA sequencing, is deemed as the safest test method. Technologies based on immunohistochemistry (IHC) are still widely used in clinical environments, next to polymerase chain reaction tests (PCR-Tests). All these tests are however expensive.

AI-based approaches, on the other hand, are hindered by the fact that some of the molecular biomarkers are hard to identify based on morphological features, which is what image-based artificial intelligence methods rely on. As a result, the accuracy that they can reach in these cases is insufficient for clinical diagnostic standards.

SUMMARY

It is an object of one or more embodiments of the present invention to provide a computer-implemented diagnostic-assistance system for medical applications which optimizes the prediction of molecular biomarkers from the morphological features present in digitized histopathology slides, in particular in whole slide images, in order to provide a computer-implemented diagnostic decision support capable of performing predictions with diagnostic relevance.

A purpose of embodiments of the present invention is achieved through a system and/or method with the features specified in one or more of the independent claims.

Preferred embodiments of the present invention with advantageous features are given in the dependent claims and the disclosure.

In the following, the solution according to embodiments of the present invention is described with respect to the claimed systems as well as with respect to the claimed methods. Features, advantages or alternative embodiments herein can be assigned to the other corresponding claimed objects and vice versa. In other words, the method can be improved with features described or claimed in the context of the corresponding system. In this case, the functional features of the methods correspond to the units and modules of the systems.

A first aspect of embodiments of the present invention provides a computer-implemented diagnostic-assistance system for medical applications, comprising: an input interface, which is configured to obtain an image dataset of a patient; an artificial intelligence entity, having an artificial intelligence neural network, ANN, which is configured to classify the images of the obtained image dataset according to a set of classes, and having a confidence module, which is configured to generate a confidence measure associated with each of the classified images; a tagging module, which is configured to generate a diagnostic signal for the patient, based on the generated confidence measures associated with the classified images, wherein the diagnostic signal for the patient is tagged as conclusive if a processed combination of the generated confidence measures fulfills a predefined condition and tagged as inconclusive if the processed combination of the generated confidence measures does not fulfill the predefined condition; and an output interface, configured to output the diagnostic signal, wherein if the diagnostic signal is conclusive the classification result is released, and if the diagnostic signal is inconclusive an additional diagnostic analysis is triggered.

The input interface and/or the artificial intelligence entity and/or the tagging module and/or the output interfaces are broadly understood as entities capable of acquiring, obtaining, receiving or retrieving image data and delivering it for further processing. Each of them, or parts thereof, may therefore contain, at least, a central processing unit, CPU, and/or at least one graphics processing unit, GPU, and/or at least one field-programmable gate array, FPGA, and/or at least one application-specific integrated circuit, ASIC and/or any combination of the foregoing. Each of them may further comprise a working memory operatively connected to the at least one CPU and/or a non-transitory memory operatively connected to the at least one CPU and/or the working memory. Each of them may be implemented partially and/or completely in a local apparatus and/or partially and/or completely in a remote system such as by a cloud computing platform.

All of the elements of the diagnostic assistance system may be realized in hardware and/or software, cable-bound and/or wireless, and in any combination thereof. Any of the elements may comprise an interface to an intranet or the Internet, to a cloud computing service, to a remote server and/or the like.

In particular, the diagnostic assistance system may be implemented partially and/or completely in a local apparatus, e.g. a computer, in a system of computers and/or partially and/or completely in a remote system such as a cloud computing platform.

An image dataset broadly describes any information that can be used for further processing and analysis in medical applications. In the context of prediction of molecular alterations in cancerous tumors, the image dataset might consist of on or more images of tissue samples of a patient acquired through surgery or biopsy and artificially stained using any of the staining methods used in the field. Some of these stained tissue samples might comprise a selected sub-image portion or a crop of a larger image, where segmentation has been applied. An image dataset can also comprise metadata. In the following, image dataset, image data or images will indistinctly be used to describe information in image form or as metadata.

An artificial intelligence entity shall be understood to comprise or consist of an artificial neural network and, possibly, a principal component analysis (PCA) and partial least squares (PLS). Whenever herein an artificial neural network is mentioned, it shall be understood as a computerized entity able to implement different data analysis methods broadly described under the terms artificial intelligence, machine learning, deep learning or computer learning. The artificial neural network can be a generative adversarial network (GAN), a convolutional neural network (CNN) or any other neural network.

A set of classes refers herein to the possible outputs of the artificial neural network. In most of the applications, the set of classes is predetermined. For instance, in the detection of a certain molecular biomarker, a class may indicate the presence or the absence of the certain molecular biomarker.

A confidence measure (or confidence level, or certainty score or trust level) is to be understood as a numerical value or a collection of numerical values (e.g. a vector) that indicate, according to a model or algorithm, the degree of certainty or uncertainty with which a certain prediction is made and/or the quality of a certain classification. The confidence measure can be based on the output layer of the artificial neural network or obtained using more sophisticated statistical tools.

A diagnostic signal may comprise an indication that a specific disease or condition may be or even is present in a patient. In the context of prediction of molecular biomarkers in cancerous tumors, the diagnostic signal can indicate the presence of a biomarker or the absence thereof. A conclusive diagnosis is to be understood as a diagnosis with enough prediction confidence to be used in the clinical workflow. In contrast, an inconclusive diagnosis is to be understood as a diagnosis with not enough confidence to be incorporated into the clinical workflow.

A second aspect of embodiments of the present invention provides a computer-implemented diagnostic-assistance method for medical applications, comprising the following steps: (a) obtaining an image dataset of a patient; (b) classifying the images of the image dataset according to a set of classes; (c) generating a confidence measure associated with each classified image of the image dataset; (d) generating a diagnostic signal for the patient, based on the generated confidence measures associated with the classified images, wherein the diagnostic signal for the patient is tagged as conclusive if a processed combination of the generated confidence measures fulfills a predefined condition and tagged as inconclusive if the processed combination of the generated confidence measures does not fulfill the predefined condition; and (e) outputting the diagnostic signal, wherein if the diagnostic signal is conclusive the classification result is released, and if the diagnostic signal is inconclusive an additional diagnostic analysis is triggered.

In particular, the method according to the second aspect of embodiments of the present invention may be carried out with the computer-implemented diagnostic-assistance system according to the first aspect of embodiments of the present invention. The features and advantages disclosed herein in connection with the computer-implemented diagnostic-assistance system are therefore also disclosed for the method, and vice versa.

According to a third aspect, embodiments of the present invention provide a computer program product comprising executable program code configured to, when executed, perform the method according to the second aspect of embodiments of the present invention.

According to a fourth aspect, embodiments of the present invention provide a non-transient and/or non-transitory computer-readable data storage medium comprising executable program code configured to, when executed, perform the method according to the second aspect of embodiments of the present invention.

The non-transient computer-readable data storage medium may comprise, or consist of, any type of computer memory, in particular semiconductor memory such as a solid-state memory. The data storage medium may also comprise, or consist of, a CD, a DVD, a Blu-Ray-Disc, an USB memory stick or the like.

According to a fifth aspect, embodiments of the present invention provide a data stream comprising, or configured to generate, executable program code configured to, when executed, perform the method according to the second aspect of embodiments of the present invention.

One of the main ideas underlying embodiments of the present invention is to provide a computer-based support system for medical applications, in particular for the prediction of morphological molecular alterations in high-resolution microscopy data of tumor tissues, in order to assist in the diagnosis of related cancer types and eventually in the prognosis and treatment options. The system is configured to obtain, receive or acquire a set of image data of a patient and classify each image of the dataset with a pre-trained artificial neural network. Each classified image is assigned a confidence measure, which is then elevated to a confidence measure associated with all the images of the patient. If this confidence measure fulfils a certain condition (e.g. it is above a predefined threshold), a conclusive diagnosis for the patient is generated. If this confidence measure does not fulfil the certain condition (e.g. it is at or below the predefined threshold), the diagnosis for that particular patient is inconclusive. If the diagnostic signal is conclusive, the classification result is released as an output signal. If, in contrast, the diagnostic signal is inconclusive, an additional diagnostic analysis is triggered.

In particular, for the prediction of molecular alterations, the conclusive diagnosis may be a safe prediction about the presence or absence of a molecular biomarker.

The system as described above affords a simple implementation of a computer-based assistance diagnosis method. In a first step, a set of image data of a patient is obtained. These image data is processed by a pre-trained artificial neural network, which generates a classification based on a predetermined set of classes. In another step, a confidence measure is generated for each classified image. Based on the generated confidence measure associated with each of the classified images, a confidence measure associated with all the images of a patient is inferred and a diagnostic signal for the patient is generated, which can be conclusive if the confidence measure fulfills a certain condition (e.g. the confidence measure is above a predefined threshold) and inconclusive if the confidence measure does not fulfill the certain condition (e.g. the confidence level is at or below the predefined threshold). If the diagnostic signal is conclusive, the classification result is released. If, in contrast, the diagnostic signal is inconclusive, an additional diagnostic analysis is triggered.

One advantage of embodiments of the present invention is that the performance of the artificial neural network as a prediction tool for molecular alterations is enhanced by selecting those cases where a prediction can be made with confidence. This way artificial intelligence is used where it can have clinically significant impact. Embodiments of the present invention therefore are an improvement over artificial intelligence approaches without a confidence estimation.

Another advantage of one or more embodiments of the present invention is that it is more efficient than prediction systems based on IHC, NGS or PCR tests. These tests are task-specific, while the system and method of embodiments of the present invention can use standard H&E slides, which are part of the medical workflow. The more expensive IHC, NGS or PCR tests can be reserved for those cases where a prediction with artificial intelligence methods cannot be made with confidence. In other words, embodiments of the present invention cut the costs of IHC, NGS or PCR tests for those patients where a prediction can be made with the more affordable H&E images. This leads to an optimization of resources.

A further advantage of embodiments of the present invention is that, since one or more embodiments of the present invention rely on the morphological features that can be extracted from H&E images, the image dataset can be used for different tasks. This makes embodiments of the present invention versatile, as it can deal with predictions for different molecular biomarkers in a patient without having to change the image dataset.

Advantageous embodiments and further developments follow from the dependent claims as well as from the description of the different preferred embodiments illustrated in the accompanying figures.

According to some of the embodiments, refinements, or variants of embodiments, the obtained image dataset comprises a set of digitized images, preferably a set of histopathological whole slide images of a patient. Whole slide images are microscopy magnified slides containing hundreds of thousands of pixels in each dimension, which leads to a precision of micrometers. These images are very rich in morphological information and are therefore especially suited to be processed with artificial intelligence and machine learning tools, especially when it comes to the identification and classification of molecular alterations, which are subtle and therefore hard to identify using non-AI-based methods.

According to some of the embodiments, refinements, or variants of embodiments, the whole slide images are generated from stained slides of hematoxylin-eosin stain. As already mentioned above, stained slide of hematoxylin and eosin are part of the clinical workflow. They are therefore easily available and do not need to be generated for each analysis. Furthermore, they can be employed for different tasks.

According to some of the embodiments, refinements, or variants of embodiments, the artificial intelligence neural network, ANN, is a convolutional neural network, CNN. Given the huge amount of data contained in whole slide images, CNNs are in particular very efficient when dealing with image analysis and pattern recognition. Preferred embodiments of the present invention use powerful, efficient and sophisticated CNNs such as EfficientNet-B0.

According to some of the embodiments, refinements, or variants of embodiments, the convolutional neural network CNN is trained end-to-end with training data, said training data not having auxiliary labels, also referred to as annotations. As already mentioned above, whole slide images contain a huge amount of data. Depending on the task at hand, some parts of the image might be more relevant than others. In some AI-based methods the regions of interest of an image are identified with a trained segmentation model. Depending on the task, this annotation can be rather demanding. Recent developments in the field, to which the inventors have contributed, show that one can eliminate this segmentation step and have an annotation-free, end-to-end trainable CNN, with results competitive with the more conventional methods involving annotations. In some preferred embodiments of the present invention, the k-Siamese CNN architecture introduced in M. Teichmann, A. Aichert, H. Bohnenberger, P. Strobel and T. Heimann, "End-to-end Learning for Image-based Detection of Molecular Alternations in Digital Pathology" (https://arxiv.org/pdf/2207.00095) is used.

According to some of the embodiments, refinements, or variants of embodiments, the convolutional neural network CNN is configured to receive as input the obtained image dataset and, additionally, non-image-based information of the patient. The augmentation of the dataset with patient-specific meta-data, such as gender, age and/or previous medical diseases and conditions can increase the performance of the CNN.

According to some of the embodiments, refinements, or variants of embodiments, the set of classes comprises types of molecular biomarkers for cancer detection, in particular MSI and/or Lynch syndrome and/or epidermal growth factor receptor (EGFR) and/or Kirsten rat sarcoma viral oncogene homolog (KRAS) and/or Programmed death-ligand 1 (PD-L1). Molecular biomarkers are biological molecules in fluids (e.g. blood) or tissue indicatives of an abnormal process, a condition or a disease. Molecular biomarkers for cancer detection are indicatives of the presence of certain classes of cancers and their evolution state. Thus, they are an essential tool in order to reach a diagnosis, and a patient-specific prognosis and treatment recommendations.

According to some of the embodiments, refinements, or variants of embodiments, the set of classes (C1-C4) comprise a classifier for MSI, wherein the image dataset comprises images obtained from a patient with colorectal cancer. By the set of classes (C1-C4) comprising a classifier for MSI, the medical diagnosis assistance system as a whole can be considered to be configured to be a classifier for MSI. Microsatellite instability (MSI) is the condition of genetic hypermutability that results from impaired DNA mismatch repair. A detection of MSI therefore indicates abnormal functioning of the mismatch repair, which is associated with a number of cancers, such as colon cancer, gastric cancer, endometrium cancer, ovarian cancer, hepatobiliary tract cancer, urinary tract cancer, brain cancer or skin cancers. Most prevalently, MSI is associated with colorectal cancer. Around 15% of patients with colon cancer are MSI-positive. Patients with colorectal tumors are thus routinely tested for MSI.

According to some of the embodiments, refinements, or variants of embodiments, the diagnostic signal is based on a weighted average calculated over all classified images of the obtained image dataset, wherein the weights used to calculate the weighted average are based on the confidence measures associated with the classified images.

According to some of the embodiments, refinements, or variants of embodiments, the diagnostic signal is further based on patient-specific non-image-based information. As discussed above, in some embodiments meta-data of the patient can be used together with the image data as input of the artificial neural network. The use of meta-data of the patient can also be used once the confidence level of the images is known and a diagnosis signal has to be generated. Patient-specific information, e.g. the occurrence of a previous cancer, is relevant information when generating a diagnosis.

According to some of the embodiments, refinements, or variants of embodiments, the confidence module comprises a softmax unit, which is configured to determine at least one confidence measure based on a softmax action selection and/or comprises a Bayesian unit, which is configured to determine the at least one confidence measure based on Bayesian inference.

A possible confidence measure associated e.g. to the detection or absence of a molecular biomarker is the output of the logit function, which can be implemented in the final layer of the artificial neural network. A more sophisticated confidence measure can be computed on the basis of a probabilistic interpretation of the output of the logit function.

In a softmax action selection a statistical approach is taken. One can e.g. assume that the logits output by the logit function follow a Boltzmann distribution and then associate the confidence measure to a likelihood found using logistic regression. Another possibility is to use Bayesian inference. There are different Bayesian-based approaches available, which are purported to yield very strong confidence levels associated with the predictions of artificial neural networks.

According to some of the embodiments, the additional diagnostic analysis is an IHC-based test and/or a PCR-based test and/or a NGS-based test. In other words, patients whose diagnostic signals are tagged as inconclusive by the system of the first aspect of embodiments of the present invention can be tested using state-of-the-art non-IA-based methods.

According to some of the embodiments, the additional diagnostic analysis is configured to generate a further diagnostic signal. Therefore, the patients whose diagnostic signals are tagged as inconclusive by the system of the first aspect of embodiments of the present invention obtain another diagnosis based on alternative methods.

According to some of the embodiments, the computer-implemented diagnostic-assistance system is part of a medical diagnosis assistance system, which further comprises an IHC-module and a global output interface. The IHC-module is configured to predict the presence of the molecular biomarker for those patients whose diagnostic signal was tagged as inconclusive by the computer-implemented diagnostic-assistance system and generate a further diagnostic signal.

The IHC-module is to be understood as an entity capable of performing not just IHC tests, but also PCR tests, NGS and other state-of-the-art tests not based on artificial intelligence implementations. The capabilities of the IHC-module may depend on the patient and on the task at hand.

In other words, those patients where the molecular biomarkers are not clearly identified through morphological aspects, and as a result cannot be predicted with high enough confidence by an image-based artificial intelligence neural network, have to be diagnosed with state-of-the-art tests to reach a second diagnosis signal. This leads to an optimized use of resources, since the prediction with AI-based methods is considerably less expensive than IHC, PCR or NGS tests, which are only employed when the AI-based methods are not reliable enough. The medical diagnosis assistance system can be embedded inside a diagnostic decision support system (DDSS) to aid the human decision-making in the clinical and/or medical workflow.

Although here, in the foregoing and also in the following, some functions are described as being performed by modules, it shall be understood that this does not necessarily mean that such modules are provided as entities separate from one another. In cases where one or more modules are provided as software, the modules may be implemented by program code sections or program code snippets, which may be distinct from one another but which may also be interwoven or integrated into one another.

Similarly, in cases where one or more modules are provided as hardware, the functions of one or more modules may be provided by one and the same hardware component, or the functions of several modules may be distributed over several hardware components, which need not necessarily correspond to the modules. Thus, any apparatus, system, method and so on which exhibits all of the features and functions ascribed to a specific module shall be understood to comprise, or implement, said module. In particular, it is a possibility that all modules are implemented by program code executed by a computing device, for example a server or a cloud computing platform.

The above embodiments and implementations can be combined with each other as desired, as far as this is reasonable.

Further scope of the applicability of the present method and apparatus will become apparent from the following figures, detailed description and claims. However, it should be understood that the detailed description and specific examples, while indicating preferred embodiments of the invention, are given by way of illustration only, since various changes and modifications within the spirit and scope of the present invention will become apparent to those skilled in the art.

BRIEF DESCRIPTION OF THE DRAWINGS

Aspects of the present disclosure will be better understood with reference to the following figures. The components in the drawings are not necessarily to scale, emphasis being placed instead upon clearly illustrating the principles of the present disclosure. Parts in the different figures that correspond to the same elements have been tagged with the same reference numerals.

In the figures.

The figures might not be to scale and certain components can be shown in generalized or schematic form in the interest of clarity and conciseness. In some instances, well-known structures and devices are shown in block diagram form in order to avoid obscuring the concepts of the present invention. Likewise, the numeration of the steps in the methods are meant to ease their description. They do not necessarily imply a certain ordering of the steps. In particular, several steps may be performed concurrently.

DETAILED DESCRIPTION

The detailed description includes specific details for the purpose of providing a thorough understanding of the present invention. However, it will be apparent to those skilled in the art that the present invention may be practised without these specific details.

Figure 1:
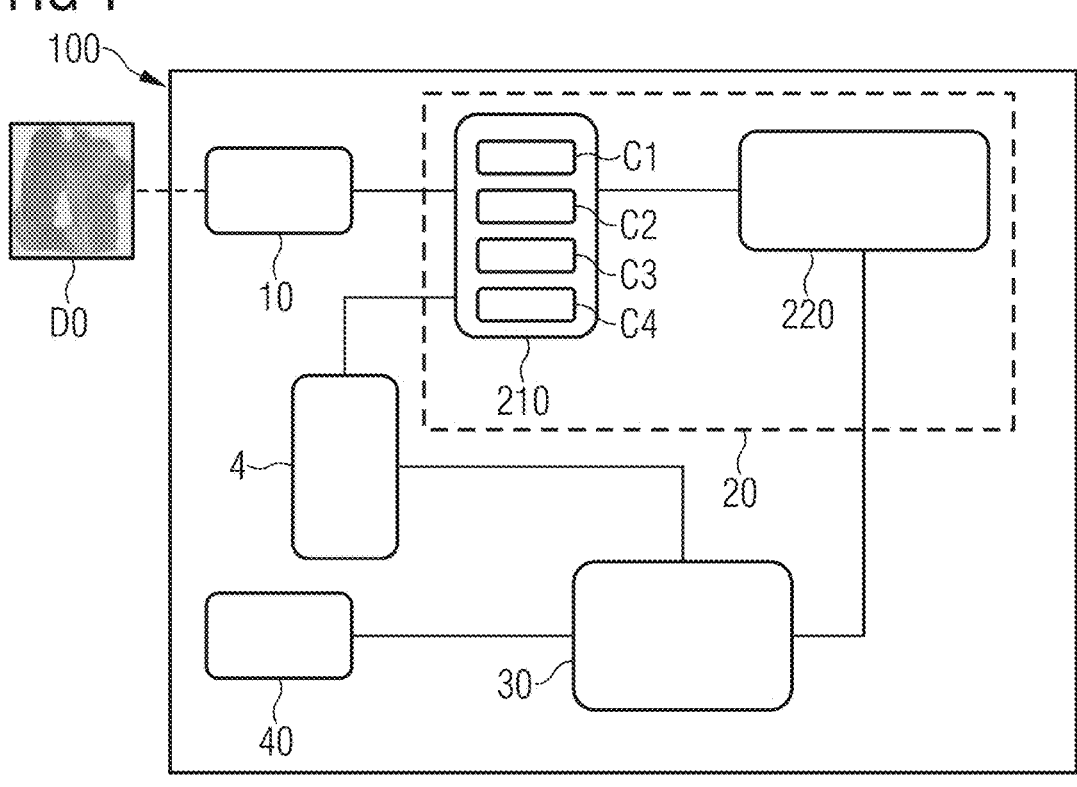
FIG. 1 is a schematic depiction of a computer-implemented diagnostic-assistance system for medical applications according to an embodiment of the present invention.

FIG. 1 shows a schematic illustration of a computer-implemented diagnostic-assistance system 100 for medical applications according to an embodiment of the present invention. Whenever a concrete example might be useful to illustrate how the system operates, we will use as application the prediction of the microsatellite instability (MSI) in samples of colorectal cancer. However, it should be understood that this particular example does not limit the scope of the invention.

The computer-implemented diagnostic-assistance system 100 comprises an input interface 10, an artificial intelligence entity 20, a tagging module 30 and an output interface 40.

The input interface 10 is broadly understood as any entity capable of acquiring, obtaining or receiving image data DO and delivering it for further processing. The image data DO may comprise magnified microscopy data of tumor tissues, preferably whole slide imaging of formalin-fixed paraffin-embedded (FFPE) slides with hematoxylin and eosin (H&E) stained tissue samples. This image data DO might comprise portions of whole slide images generated, e.g., through segmentation and/or tessellation and/or any other procedure to select a part of an image. The image data DO might also comprise more than one image of a patient.

The artificial intelligence entity 20 is to be broadly understood as any entity capable of processing data. The artificial intelligence entity 20 in FIG. 1 comprises an artificial intelligence neural network 210 and a confidence module 220.

The artificial intelligence neural network 210 is preferably a convolutional neural network. Preferred embodiments of the present invention use powerful, efficient and sophisticated CNNs such as EfficientNet-B0. The artificial intelligence neural network 210 is implemented with an algorithm. The inventors have realized that in particular the algorithm described in M. Teichmann, A. Aichert, H. Bohnenberger, P. Strobel and T. Heimann, "End-to-end Learning for Image-based Detection of Molecular Alternations in Digital Pathology" (https://arxiv.org/pdf/2207.00095) as a k-Siamese CNN architecture yields optimal results. The k-Siamese CNN is an end-to-end trainable CNN free of task-specific auxiliary labels, also referred to as annotations. The k-Siamese CNN does not require a segmentation step, in which regions of interest of whole slide images (WSI) are sorted out and possibly further annotated. This CNN takes as input a set of smaller tiles (e.g., with 244 pixels in each dimension) of the WSIs, which are generated through tessellation in an unsupervised way. For each WSI a subset of k smaller tiles is randomly selected and processed in parallel by k CNNs with the same weights. Each CNN outputs a feature vector, such that for each whole slide image one obtains k feature vectors. These k feature vectors are then combined or aggregated and used to output a single prediction signal for each WSI. An overall prediction for each patient is obtained by averaging over the predictions of each WSI.

In the particular example of MSI prediction, after the tessellation k randomly chosen small tiles of a WSI are processed simultaneously by k copies of a CNN, i.e., k CNN with the same parameters, in particular with the same weight selection. Each CNN outputs a feature vector that gives a prediction for the presence or absence of MSI in the corresponding tile of the WSI. The whole feature vectors are combined to indicate the presence or absence of MSI in that particular WSI. In a hypothetical case, in some of the WSI, MSI will be predicted, while in some other WSI the absence thereof will be predicted. A global prediction can be made by taking into account the prediction of each WSI.

The artificial intelligence neural network 210 is trained using a fine-tuning approach starting from the standard EfficientNet weights. The base learning-rate is set at $2 \times 10^{-5}$ and the batch-size is 6. The normalized learning-rate is obtained as the product of the base-learning rate and the batch-size. The model is trained with 72 epochs, 12 of which are warm-up epochs, during which the learning rate is linearly increased from 0 to nlr. For the remaining 60 epochs, polynomial learning rate decay is used. Data-augmentation, namely (random) brightness, contrast, saturation, hue and/or rotation is applied to each tile independently. The tiles are chosen randomly from non-overlapping parts of the images. Tiles containing only background are excluded. For training, 24 tiles per slide are used, each with a spatial resolution of $256 \times 256$ pixel. Inference is performed on 96 tiles.

The artificial intelligence neural network 210 performs a classification based on a set of classes. In the particular example of MSI prediction, the set of classes C1-C4 can be limited to a class, namely presence of MSI and absence thereof. However, more sophisticated cases are also possible. Lynch syndrome is a molecular biomarker that is also associated with colorectal cancer. The artificial intelligence neural network 210 can then be configured to perform two different tasks simultaneously, namely e.g. the prediction of MSI and Lynch syndrome. Both molecular biomarkers do not exclude each other, i.e. in some of the small tiles into which a whole slide image (WSI) has been split. There can be tumors showing MSI and Lynch syndrome, only one of them or none of them. In this example, the artificial intelligence neural network 210 can produce four different prediction outcomes, namely a prediction of a presence of both MSI and Lynch syndrome, a prediction of an absence of both MSI and Lynch syndrome, a prediction of a presence of MSI and an absence of Lynch syndrome and a prediction of an absence of MSI and a presence of Lynch syndrome.

The prediction outcomes of each tile of a WSI can then be combined to reach a prediction for the respective WSI and then at a global level for all WSIs, indicating the presence or absence of the molecular biomarkers such as the MSI and Lynch syndrome in the obtained image dataset DO.

The confidence module 220 is configured to assign a confidence measure to each of the predictions reached by the artificial intelligence neural network 210. As discussed above, this confidence level or confidence measure can be obtained using different techniques, from the raw output of the logit layer of the artificial neural network 210 to more sophisticated implementations, e.g., statistically-based approaches or Bayesian-based approaches. In the particular embodiment with a k-Siamese CNN mentioned above, the confidence module 220 may assign a confidence measure to the output of each k CNN of each WSI. However, other implementations are possible, e.g., to assign a confidence measure to the prediction for each WSI. Partial or combined implementations of these approaches are also possible. Depending on the particular implementation, the confidence module 220 may assign a confidence measure to all the k tiles of a WSI, to only a subset thereof, or a global confidence measure to each WSI. Whenever confidence measures are generated for individual tiles of a WSI, the confidence module 220 is configured to calculate a weighted average for them.

With the combination and interplay of the functionalities of the artificial intelligence neural network 210 and the confidence module 200, the artificial intelligence entity 20 is configured to generate a prediction with an associated confidence measure for each obtained and processed WSI.

The tagging module 30 is configured to generate a diagnostic signal for a patient, based on the generated confidence measures associated with each of the classified images. This confidence measure is elevated to a global trust level for the whole processed images of a patient. In some of the preferred embodiments, this global trust level may be generated based on a weighted average over the confidence measures of the WSIs of the patient. This calculated global trust level is a numerical quantity. If the global trust level for a patient fulfills a certain condition (e.g. it is above a predetermined threshold value), the tagging module 30 tags the diagnostic result for that patient as conclusive. If, in contrast, the global trust level for a patient does not fulfill the condition (e.g. it is at or below the predetermined threshold value), the tagging module 30 tags the diagnostic result for that patient as inconclusive. In the example of MSI prediction, a conclusive diagnosis for a patient does either predict the presence of MSI or predict the absence of MSI in the tumor tissue samples of the patient. The criterion behind the choice of the condition to be fulfilled may be based on current standards that define clear-cut predictions in the clinical workflow, such that the predictions provided by the system of embodiments of the present invention can be used in clinical pathway decisions.

The output interface 40 of the system 100 is broadly understood as any entity capable of generating a diagnostic signal based on the information acquired from the tagging module 30 of the system 100. If the generated diagnostic signal has been tagged as conclusive, the output interface 40 of the system 100 is adapted to release the classification result of the tagging module 30. If instead the diagnostic signal is inconclusive an additional diagnostic analysis can be automatically triggered by the system 100.

If the computer-implemented diagnostic-assistance system 100 is implemented as part of a computer-assisted clinical diagnostic function embedded inside a diagnostic decision support system (DDSS), the output interface 40 of the system 100 can present the diagnostic signal on a user interface such as a website, an application, a software or an electronic health records (EHR) front-end interface.

In a preferred embodiment as illustrated in FIG. 1, the computer-implemented diagnostic-assistance system 100 further comprises a meta-data module 4, which is configured to store non-image-based information of the same patient from which the image dataset D0 has been obtained. This information may comprise age and/or gender and/or parts of the patient's medical record. The meta-data module 4 of the system 100 may comprise at least a non-transient computer-readable data storage medium which may comprise, or consist of, one or more hard drives, SSDs, external hard disk drives, optical media such as CDs and/or a DVDs, Blu-Ray-Discs, flash media such as thumbdrives and USB memory stick or any device able to provide a storage unit for a database and/or a data warehouse with a fast and consistent input/output performance. The meta-data module 4 of the system 100 may also comprise a cloud database. The meta-data module 4 may further comprise a central processing unit, CPU and/or at least one field-programmable gate array, FPGA, and/or at least one application-specific integrated circuit, ASIC and/or any combination of the foregoing together with executable program code. Each of them may be implemented partially and/or completely in a local apparatus such as a computer or a tablet, and/or partially and/or completely in a remote system, such as by a cloud computing platform. The meta-data module 4 of the system 100 may be realized in hardware and/or software, cable-bound and/or wireless, and in any combination thereof. It may comprise an interface to an intranet or the Internet, to a cloud computing service, to a remote server and/or the like. In particular, it may be able to retrieve data from electronic health records (EHR).

The meta-data module 4 of the system 100 may supply stored non-image information of a patient to the artificial intelligence entity 20, which is then inputted in the artificial intelligence neural network 210 together with the obtained image dataset D0 of the same patient. Likewise, the meta-data module 4 may also supply non-image information to the tagging module 30, which is then processed and used to reach a diagnosis.

Figure 2:
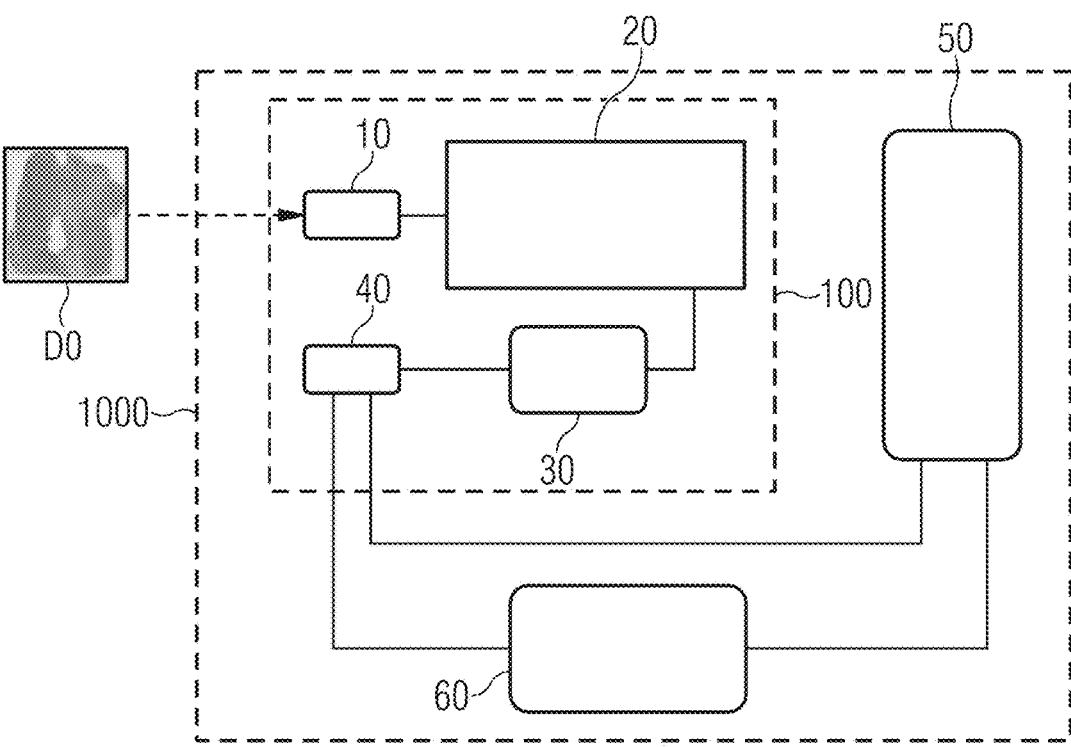
FIG. 2 is a schematic illustration of a medical diagnosis assistance system according to another embodiment of the present invention.

FIG. 2 shows a schematic illustration of a medical diagnosis assistance system 1000 according to another embodiment of the present invention. This medical diagnosis assistance system 1000 comprises a computer-implemented diagnostic-assistance system 100 such as described in FIG. 1, and an IHC-module 50.

As illustrated in FIG. 1, the computer-implemented diagnostic-assistance system 100 is configured to process whole slide images based on an H&E dataset of a patient. The tagging module 30 of the system 100 is configured to tag the resulting diagnostic signal as conclusive or inconclusive. A conclusive diagnosis can be incorporated to the clinical workflow to assist in the taking of a clinical decision thus affecting e.g. the prognosis and treatment options of the patient. An inconclusive diagnostic signal indicates that image-based AI methods cannot reach a sufficient confidence level for the investigated molecular biomarkers. This can be the case because, in a particular patient, the molecular alterations do not lead to detectable morphological changes. Tests of the system 100 have shown that this is indeed the case in certain patients, whereas molecular alterations in other patients leave traces in the form of morphological changes, which are used by the artificial intelligence neural network 210 of the system 100 to infer the presence of a molecular biomarker. A patient whose diagnostic signal is inconclusive according to the tagging module 30 can be diagnosed with the more expensive state-of-the-art tests, such as IHC, NGS or PCR.

The IHC-module 50 is configured to predict the presence of the molecular biomarker for those patients whose diagnostic signal has been tagged as inconclusive by the computer-implemented diagnostic-assistance system 100 and is configured to generate a further diagnostic signal. As mentioned above, the capabilities of the IHC-module 50 are not restricted to perform IHC tests, but they should be understood to cover a broad spectrum of different tests, which are decided by the expert in charge of the patient and thus may differ depending on the task at hand and on the patient. The IHC-module 50 schematically comprises, rather generically, a module able to implement analysis based on more complex tests, such as immunohistochemistry (IHC), but also next-generation sequencing (NGS) and polymerase chain reaction tests (PCR-Tests).

The computer-implemented diagnostic-assistance system 100 and the IHC-module 50 are cable-bound and/or wireless connected. In some preferred embodiments, the output interface 40 of the system 100 can be further configured to send a signal to the IHC-module 50, e.g. to send a file identifying the patients which could not be conclusively diagnosed by the system 100. This signal information is then processed in the IHC-module 50 and eventually a further diagnostic signal for those patients based on IHC tests and/or NGS and/or PCR tests, to name some of the most common tests, is released by the IHC-module 50.

The computer-implemented diagnostic-assistance system 100 thus filters the patients where these tests can be spared and a diagnosis can be made only by processing the more affordable and versatile H&E (hematoxylin-eosin) images. The system 100 has a competitive performance compared to a conventional IHC-based approach. In some cases, the system 100 according to embodiments of the present invention even outperforms the prediction capabilities of IHC-based tests. For instance, for the prediction of MSI, the sensitivity of the prediction according to some of the embodiments of the computer-implemented diagnostic-assistance system 100 ranges between 91% and 97%, while an IHC-based analysis yields only 88%. For the specificity, the prediction according to the same embodiments of the computer-implemented diagnostic-assistance system 100 reaches 98%, while an IHC-based analysis yields only 94%.

In some embodiments, the medical diagnosis assistance system 1000 allows for a validation of the computer-implemented diagnostic-assistance system 100. This can be done by sampling a selection of the patients with a conclusive diagnostic result, which can be reported to the IHC-module 50 in order to be further processed using state-of-the-art tests. A validation unit 60 of the medical diagnosis assistance system 1000 may be configured to compare the (conclusive) diagnostic signal released by the computer-implemented diagnostic-assistance system 100 with the further diagnostic signal.

The medical diagnosis assistance system 1000 may be embedded inside a diagnostic decision support system (DDSS) to assit the human decision-making in the clinical and/or medical workflow. In this case, the output interface 40 of the system 100 can present the diagnostic signal on a user interface such as a website, an application, a software or an electronic health records (EHR) front-end interface.

Figure 3:
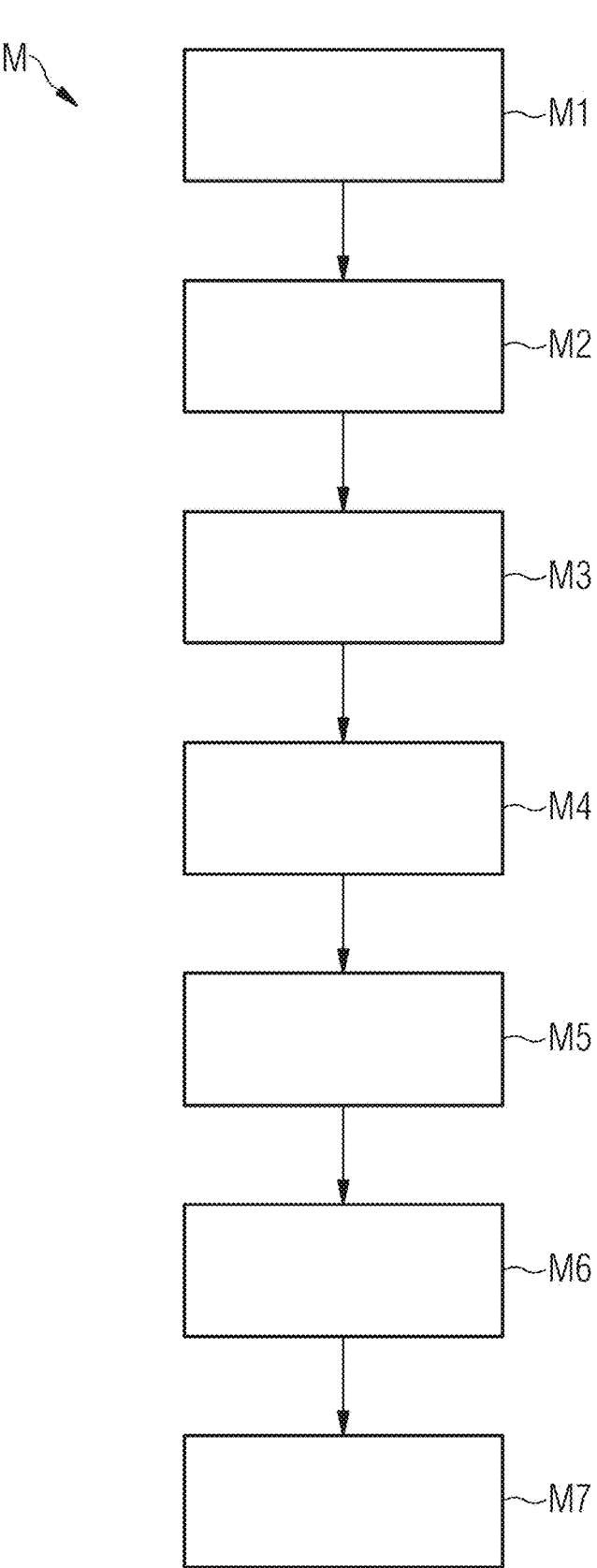
FIG. 3 is a block diagram showing an exemplary embodiment of a computer-implemented diagnostic-assistance method for medical applications.

FIG. 3 is a block diagram showing an exemplary embodiment of a computer-implemented diagnostic-assistance method M for medical applications, to be applied preferably with the computer-implemented diagnostic-assistance system 100 described in FIG. 1. One step M1 comprises obtaining an image dataset D0 of a patient, preferably comprising whole slide images (WSI) generated from H&E stained slides of tumor tissue of a patient. In another step M2, the images of the image dataset D0 are classified according to a set of classes C1-C4.

In a further step M3, each classified image is assigned a confidence measure, which gauges the reliability of the classification. In another step M4, a diagnostic signal is generated for the patient, based on the generated confidence measures of the classified images. The diagnostic signal for the patient is tagged as conclusive if the confidence measure fulfills a certain condition, e.g. it is above a predefined threshold, and tagged as inconclusive if the confidence measure does not fulfill the conditions, e.g. it is at or below the predefined threshold. In the example of MSI detection discussed previously, a conclusive diagnosis can either indicate the presence of MSI with certainty or the absence of MSI with certainty. In another step M5 this diagnostic signal is outputted to be further processed. If the diagnosis for the patient is conclusive it can be used e.g. as assistance for decision taking in the clinical pathway. If the diagnosis for the patient is inconclusive, a further diagnostic analysis with other methods can be triggered.

In some embodiments of the method, a further step M6 is foreseen, in which information about the patients inconclusively diagnosed is sent out in order to perform additional tests that should eventually lead to a further diagnostic signal for those patients. In yet some embodiments of the method, another step M7 is foreseen, in which the conclusive diagnoses can be validated, for instance by sampling a number of patients with conclusive diagnoses to be tested and further diagnosed using other methods such as IHC, NGS or PCR. The diagnostic signals can then be compared and the diagnostic results provided by the method according to embodiments of the present invention can thus be validated.

Figure 4:
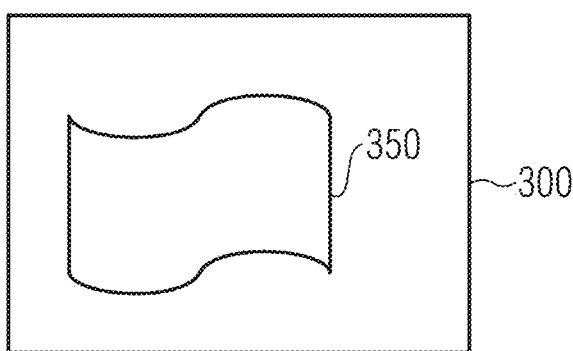
FIG. 4 is a schematic block diagram illustrating a computer program product according to an embodiment of the third aspect of the present invention.

FIG. 4 shows a schematic block diagram illustrating a computer program product 300 according to an embodiment of the third aspect of the present invention. The computer program product 300 comprises executable program code 350 configured to, when executed, perform the method according to any embodiment of the second aspect of the present invention, in particular as has been described with respect to the preceding figures.

Figure 5:
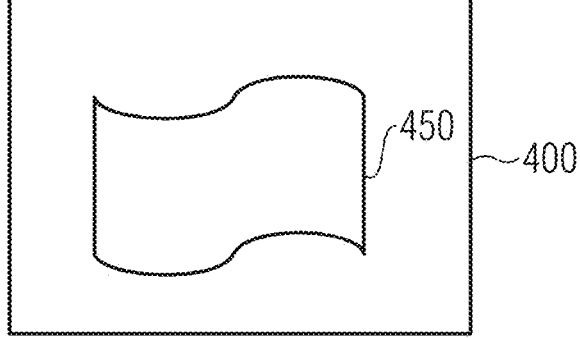
FIG. 5 is a schematic block diagram illustrating a non-transitory computer-readable data storage medium according to an embodiment of the fourth aspect of the present invention.

FIG. 5 shows a schematic block diagram illustrating a non-transitory computer-readable data storage medium 400 according to an embodiment of the fourth aspect of the present invention. The data storage medium 400 comprises executable program code 450 configured to, when executed, perform the method according to any embodiment of the second aspect of the present invention, in particular as has been described with respect to the preceding figures.

The non-transient computer-readable data storage medium may comprise, or consist of, any type of computer memory, in particular semiconductor memory such as a solid-state memory. The data storage medium may also comprise, or consist of, a CD, a DVD, a Blu-Ray-Disc, an USB memory stick or the like.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the present invention has been shown and described with respect to certain example embodiments, equivalents and modifications will occur to others skilled in the art upon the reading and understanding of the specification. The present invention includes all such equivalents and modifications and is limited only by the scope of the appended claims.

The previous description of the disclosed embodiments are merely examples of possible implementations, which are provided to enable any person skilled in the art to make or use the present invention. Various variations and modifications of these embodiments will be readily apparent to those skilled in the art, and the generic principles defined herein may be applied to other embodiments without departing from the spirit or scope of the present disclosure. Thus, the present invention is not intended to be limited to the embodiments shown herein but it is to be accorded the widest scope consistent with the principles and novel features disclosed herein. Therefore, the present invention is not to be limited except in accordance with the following claims.

What is claimed is:

1. A computer-implemented diagnostic-assistance system for medical applications, the computer-implemented diagnostic-assistance system comprising:

at least one processor configured to execute computer program code to cause the computer-implemented diagnostic-assistance system to implement an artificial intelligence entity having an artificial intelligence neural network and a confidence module, the artificial intelligence neural network configured to classify images of an image dataset of a patient according to a set of classes, and the confidence module configured to generate a confidence measure associated with each of the classified images;

a tagging module configured to generate, for the patient, a diagnostic signal based on the confidence measures associated with the classified images, wherein the diagnostic signal for the patient is tagged as conclusive in response to a processed combination of the confidence measures fulfilling a condition, and the diagnostic signal for the patient is tagged as inconclusive in response to the processed combination of the confidence measures not fulfilling the condition; and an output interface configured to output the diagnostic signal, wherein a result of the classification is released in response to the diagnostic signal being tagged as conclusive, an additional diagnostic analysis is triggered in response to the diagnostic signal being tagged as inconclusive, the additional diagnostic analysis includes at least one of an IHC-based test or a PCR-based test, and the additional diagnostic analysis is configured to generate a further diagnostic signal.

2. The computer-implemented diagnostic-assistance system according to claim 1, wherein the image dataset comprises a set of digitized images.

3. The computer-implemented diagnostic-assistance system according to claim 2, wherein the set of digitized images includes a set of histopathological whole slide images of the patient, and histopathological whole slide images in the set of histopathological whole slide images are generated from stained slides of hematoxylin-eosin stain.

4. The computer-implemented diagnostic-assistance system according to claim 3, wherein the set of classes comprises types of molecular biomarkers for cancer detection.

5. The computer-implemented diagnostic-assistance system according to claim 1, wherein the artificial intelligence neural network is a convolutional neural network.

6. The computer-implemented diagnostic-assistance system according to claim 5, wherein the artificial intelligence neural network is trained end-to-end with training data, said training data not having auxiliary labels.

7. The computer-implemented diagnostic-assistance system according to claim 1, wherein the artificial intelligence neural network is configured to receive, as input, the image dataset and non-image-based information of the patient.

8. The computer-implemented diagnostic-assistance system according to claim 1, wherein the set of classes comprises types of molecular biomarkers for cancer detection.

9. The computer-implemented diagnostic-assistance system according to claim 8, wherein the set of classes includes a classifier for MSI, and wherein the image dataset includes images obtained from a patient with colorectal cancer.

10. The computer-implemented diagnostic-assistance system according to claim 8, wherein the types of molecular biomarkers for cancer detection include at least one of MSI, Lynch syndrome, EGFR, KRAS or PD-L1.

11. The computer-implemented diagnostic-assistance system according to claim 8, wherein the diagnostic signal is based on a weighted average calculated over all classified images of the image dataset, and wherein weights used to calculate the weighted average are based on the confidence measures associated with the classified images.

12. The computer-implemented diagnostic-assistance system according to claim 1, wherein the diagnostic signal is based on a weighted average calculated over all classified images of the image dataset, and wherein weights used to calculate the weighted average are based on the confidence measures associated with the classified images.

13. The computer-implemented diagnostic-assistance system according to claim 1, wherein the diagnostic signal is further based on patient-specific non-image-based information.

14. The computer-implemented diagnostic-assistance system according to claim 1, wherein at least one of the confidence module includes a softmax unit configured to determine at least one confidence measure based on a softmax action selection, or the confidence module includes a Bayesian unit configured to determine the at least one confidence measure based on Bayesian inference.

15. A medical diagnosis assistance system for predicting molecular biomarkers in tumor tissue, the medical diagnosis assistance system comprising:

the computer-implemented diagnostic-assistance system according to claim 1; wherein the medical diagnosis assistance system is configured to predict a presence of a molecular biomarker for patients whose diagnostic signal was tagged as inconclusive by the computer-implemented diagnostic-assistance system, and to generate the further diagnostic signal.

16. The computer-implemented diagnostic system according to claim 1, wherein the at least one processor is configured to execute computer program code to cause the computer-implemented diagnostic system to:

trigger the additional diagnostic analysis in response to the diagnostic signal being tagged conclusive, and validating a diagnosis of the patient based on a comparison of the diagnostic signal tagged as conclusive with the further diagnostic signal.

17. A computer-implemented diagnostic-assistance method for medical applications, the computer-implemented diagnostic-assistance method comprising:

obtaining an image dataset of a patient;

classifying images of the image dataset according to a set of classes;

generating a confidence measure associated with each classified image of the image dataset;

generating, for the patient, a diagnostic signal based on the confidence measures associated with the classified images, wherein the diagnostic signal for the patient is tagged as conclusive in response to a processed combination of the confidence measures fulfilling a condition, and the diagnostic signal for the patient is tagged as inconclusive in response to the processed combination of the confidence measures not fulfilling the condition; and outputting the diagnostic signal, wherein a result of the classifying is released in response to the diagnostic signal being tagged conclusive, an additional diagnostic analysis is triggered in response to the diagnostic signal being tagged inconclusive, the additional diagnostic analysis includes at least one of an IHC-based test or a POR-based test, and the additional diagnostic analysis is configured to generate a further diagnostic signal.

18. A non-transitory computer-readable data storage medium storing executable program code that, when executed by at least one processor at a computer-implemented diagnostic-assistance system, causes the computer-implemented diagnostic-assistance system to perform the computer-implemented diagnostic-assistance method according to claim 17.

19. A computer-implemented diagnostic-assistance system for medical applications, the computer-implemented diagnostic-assistance system comprising:

at least one processor; and a memory storing computer-executable instructions that, when executed by the at least one processor, cause the computer-implemented diagnostic-assistance system to obtain an image dataset of a patient, classify, via an artificial neural network, images of the image dataset according to a set of classes, generate a confidence measure associated with each of the classified images, generate, for the patient, a diagnostic signal based on the confidence measures associated with the classified images, wherein the diagnostic signal for the patient is tagged as conclusive in response to a processed combination of the confidence measures fulfilling a condition, and the diagnostic signal for the patient is tagged as inconclusive in response to the processed combination of the confidence measures not fulfilling the condition, and output the diagnostic signal, wherein a result of the classification is released in response diagnostic signal being tagged conclusive, an additional diagnostic analysis is triggered in response to the diagnostic signal being tagged inconclusive, the additional diagnostic analysis includes at least one of an IHC-based test or a PCR-based test, and the additional diagnostic analysis is configured to generate a further diagnostic signal.

* * * * *